United States Patent [19]
Osdene et al.

[11] 4,093,620
[45] June 6, 1978

[54] PROCESS FOR PRODUCING 2-CYANO N-SUBSTITUTED HETEROCYCLIC COMPOUNDS AND PRODUCTS PRODUCED THEREBY

[75] Inventors: Thomas S. Osdene; Edward B. Sanders, both of Richmond, Va.

[73] Assignee: Philip Morris Incorporated, New York, N.Y.

[21] Appl. No.: 694,687

[22] Filed: Jun. 10, 976

[51] Int. Cl.$^2$ .................. C07D 213/57; C07D 401/04
[52] U.S. Cl. ............................. 260/291; 260/293.52; 260/293.69; 260/293.75; 260/326.62
[58] Field of Search ................ 260/291, 294.9, 293.75, 260/293.52, 293.69

[56] References Cited
U.S. PATENT DOCUMENTS 3,886,209   5/1975   Kikumoto et al. ................ 260/309.5

OTHER PUBLICATIONS

Fieser & Fieser, Reagents for Organic Synthesis, vol. I, Wiley Pub. p. 1030, (1967).
Fieser & Fieser, Reagents for Organic Synthesis, vol. 13, Wiley Interscience Pub. pp. 260–261 (1972).
Abramovitch, Pyridine and its Derivatives, Supplement Part Three Interscience Pub. p. 800 (1974).
Abramovitch, Pyridine and its Derivatives, Supplement Part Two, Interscience Pub. pp. 115–116 (1974).

*Primary Examiner*—Alan L. Rotman

[57] ABSTRACT

The production of 2-cyano N-substituted heterocyclic compounds by a process which involves the reduction of N-substituted lactams followed by reaction of the intermediate product with cyanide is described. This process permits the production of many known and novel compounds.

10 Claims, No Drawings

PROCESS FOR PRODUCING 2-CYANO N-SUBSTITUTED HETEROCYCLIC COMPOUNDS AND PRODUCTS PRODUCED THEREBY

This invention relates to a process for the production of certain 2-cyano N-substituted heterocyclic compounds and their acid addition salts. The invention also relates to certain novel compounds which are produced by the present process. These compounds which are produced by the present process have utility as intermediates for the production of ultimate compounds of known utility.

Exemplary of these ultimate compounds are the amino acids corresponding to these cyano-heterocyclics. Their production from such cyano-heterocyclics is, for example, described in U.S. Pat. No. 3,886,209 of Kikumoto et al., the disclosure of which is incorporated herein by reference.

In addition to this general utility, the individual products of this invention are directly useful for a variety of applications, dependent upon the specific compound involved. Although usually known or apparent from the compounds themselves, representative, particular uses are detailed with greater specificity in the Examples which follow.

The 2-cyano heterocyclics of the present invention are prepared from their corresponding N-substituted lactams. These lactams exhibit the following formulae:

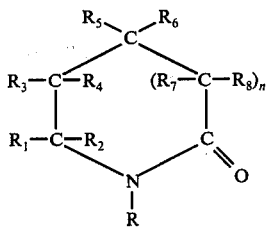

Wherein:
$n$ is 0 or 1;
R is alkyl of from 1 to 10 carbons or aryl of from 6 to 15 carbons; and each of $R_1$ through $R_8$ is H, alkyl of from 1 to 10 carbons or aryl, alkylaryl, heteroaryl or alkylheteroaryl of from 6 to 15 carbons.

As utilized in the description of these N-substituted lactams, "alkyl" embraces straight, branched and cyclic alkyl groups; groups of 1 or 2 carbons are, however, preferred. "Aryl" includes aromatics of which phenyl, tolyl, chlorophenyl and naphthyl are preferred. "Alkylaryl" means alkyl derivatives of the foregoing aryl groups, for example, benzyl. "Heteroaryl" means a nitrogen, oxygen, or sulfur substituted aryls such as pyridyl, furanyl and the like. By "alkyl heteroaryl", it is meant the corresponding analogs of the alkylaryls, such as picolyl.

The N-substituted lactams useful as starting materials for this invention are readily available and/or producible by means known in the art. Representative sources for these lactams are set forth in the examples which follow.

The production of 2-cyano heterocyclics from these N-substituted lactams proceeds by way of a two-step process. First, the lactam is contacted with a reducing agent. Thereafter, the resultant intermediate is contacted with reactive cyanide which adds to the heterocycle at the alpha position originally occupied by the carbonyl.

Both steps of this process proceed most readily when the reagents are solubilized. Consequently, it is preferred that a suitable solvent for the lactam, for example tetrahydrofuran, glyme, diglyme, dioxane or a similar oxygen-containing solvent be employed as a reaction medium to facilitate these steps. There is no criticality in the amount of solvent, but solutions of from about 5 to 15% of lactam by weight are preferred.

In the initial step, any reducing agent can be employed for contact with the N-substituted lactam. Reducing agents of very low strength, however, produce only a minor yield of reduced intermediate. Conversely, reducing agents of high strength lack selectivity in their reduction of the carbonyl group. They produce mixtures of products difficult to separate and consequently again result in lower product yeilds. An intermediate strength reducing agent such as an aluminum hydride is therefore preferred. These reagents—of which sodium aluminum hydride, sodium bis(methoxyethoxy)aluminum hydride or di-isobutylaluminum hydride have proven particularly desirable—are essentially selective in their effect upon the alpha carbonyl. They are also very efficient, often leading to yeilds of 80% or more of the 2-cyano N-substituted heterocyclics.

The amount of reducing agent which should be employed varies dependent upon its strength. Optimum amounts may therefore best be determined by monitoring the effect of increase upon ultimate yield. Ordinarily, however, from about 1.0 to 1.8 mole equivalents of reducing agent per mole of lactam is preferred. This insures relatively quantitative production of the reduced intermediate.

The conditions of reduction are essentially those customary with like steps known in the art. The temperature is oridinarily maintained below about 20° C and the reaction permitted to occur for at least about 30 minutes under an inert atmosphere such as nitrogen. Preferred conditions are temperatures between about −10° and +10° C and times of from 1 to 3 hours. These conditions allow greater control over the rate of this exothermic reaction. Once the reaction has proceeded essentially to completion, however, higher temperatures do not adversely affect this step. Indeed, it is then preferred to heat the medium to from 10° to 35° C for at least one hour to ensure maximum yield.

The second step involves addition of reactive cyanide to the medium to effect production of the 2-cyano N-substituted heterocyclics. This cyanide is most conveniently added to the reaction medium in ionic form as a salt such as potassium and sodium cyanide. It reacts in one-to-one stoichiometry with the reduced intermediate and therefore is desirably added in an amount of from 1.0 to 1.5 mole equivalents, based on the amount of lactam.

This second reaction step is also exothermic and should occur under relatively mild conditions. Thus, the reactive medium should be held at from 0° to 30° C for at least 15 minutes at the beginning of the reaction. Thereafter, however, elevated temperatures, desirably from 50° C to 110° C, are ordinarily employed for at least 15 more minutes. This ensures the maximum yield of product cyano-heterocyclics.

In a further embodiment of this invention, ammonium ion is present in the reaction medium during this second step. Small amounts of ammonium—preferably from about 0.5 to 2 mole/mole of initial lactam—have been discovered greatly to increase the yield of the 2-cyano N-substituted heterocyclics. This ammonium ion may be added in any form, although a salt, such as ammonium chloride, is preferred.

Because of the differences in solubilities between the lactams and the other reagents employed in this conversion process, it is convenient to employ a second solvent to facilitate this reaction. In a most preferred embodiment, the cyanide (and optional ammonium ion) are dissolved in water and that solution is added to the reaction medium.

After completion of this two-step synthesis, the product 2-cyano heterocyclics are readily recovered. Ordinarily, they are in the form of acid addition salts, such as their hydrochlorides. They may be used in this form, or further purified, as described. Appropriate purification procedures are, however, conventional and therefore are not further described herein except through the examples below.

EXAMPLE 1

22.1 g (0.12 M) of 1-cotinine (prepared as described by Bowman et al. in *Biochem. Prep.* 10, 36 (1963)) in 360 ml of dry tetrahydrofuran was added to a 1-liter, 3-necked flask equipped with a pressure-compensating dropping funnel, reflux condenser and a nitrogen inlet tube. The solution was cooled in an ice bath and 1.3 equivalents of a tetrahydrofuran solution of sodium aluminum hydride was added to the stirred solution under nitrogen over a one-hour period. The reaction mixture was stirred at 0° C for an additional hour and then at room temperature for 2 hours to complete reduction.

A solution of 23.4 g of potassium cyanide and 19.2 g of ammonium chloride in 200 ml of water was then added to the reaction mixture. The mixture was stirred for 30 minutes at room temperature and then heated under reflux for an additional 30 minutes.

The reaction mixture was cooled and the organic and aqueous phases separated. The aqueous phase was washed with 100 ml of ether. The ether and tetrahydrofuran phases were then combined and washed with two 100 ml portions of saturated sodium chloride solution. The organic phase was dried over sodium sulfate and filtered preparatory to removal of solvent under reduced pressure.

The residue was distilled to yield 16.1 grams (72%) of 1-5'-cyanonicotine. This compound was a thick, clear liquid having a boiling point of 120° C at 0.3 mm of Hg. It consisted of a mixture of the trans- and cis-isomers in a ratio of about 2:1. Substitution at the 5-position of the pyrrolidine ring was determined to have occurred with full retention of the chirality of the pyridine-pyrrolidine bond.

A 4% aqueous solution of di-hydrochloride salt of the 1-5'-cyanonicotine was prepared as an insecticide. The solution was applied as a spray and achieved a kill ratio of 96% when utilized for control of rose aphids.

EXAMPLE 2

26 ml of a 70% solution of sodium bis-(methoxyethoxy)aluminum hydride in benzene was added to 20 g of 1-methyl-2-pyrrolidine in 250 ml of dry tetrahydrofuran. Addition occurred over one hour at 0° C. The reaction mixture was stirred for an additional hour at 0° C and then for 2 hours at room temperature.

A solution of 29.4 g of potassium cyanide in 340 ml of water was added and the resulting mixture was stirred overnight at room temperature. Thereafter it was refluxed for 30 minutes.

The separation of products from the reaction mixture was performed as in Example 1. 10.0 g of 1-methyl-2-cyanopyrrolidine were separated by distillation. This compound had a boiling point of 57°-9° at 9.5 mm of Hg.

Hygric acid (useful for the deodorization of wool as described in U.S. Pat. No. 3,402,990 of Dewey) was then produced from the 1-methyl-2-cyanopyrrolidine. This was accomplished by refluxing a solution of 1 gram of the 1-methyl-2-cyanopyrrolidine and 10 ml of concentrated hydrochloric acid for 30 minutes. The hydrochloric acid was then removed under reduced pressure and the resulting solid was dissolved in water. The aqueous solution was adjusted to the isoelectric point with sodium hydroxide and the water then removed under reduced pressure. The sublimation of the residue gave 520 mg of pure d, l-hygric acid (1-methylpyrrolidine-2-carboxylic acid).

EXAMPLE 3

To 1.7 g of 1-phenyl-2-piperidone (prepared as set forth by Manhas and Jeng in the *J. Org. Chem.* 32, 1246, (1967) in 35 ml of tetrahydrofuran maintained at 0° C was added 40 ml of a 0.1 N solution of sodium aluminum hydride in tetrahydrofuran. Addition occurred over a one hour period. The reaction mixture was then stirred for an additional hour at 0° C and 2 hours at room temperature.

A solution of 2.28 g of potassium cyanide and 1.87 g of ammonium chloride in 75 ml of water was then added and the reaction medium was stirred for 30 minutes at room temperature followed by 30 minutes of reflux. The product, 1-phenyl-2-cyanopiperidine, was then isolated by distillation to yield 0.88 mg of a clear, colorless liquid having a boiling point of 125°-128° at 0.9 mm. The infrared spectrum of 1-phenyl-2-cyanopiperidine exhibits a band at 2220 cm$^{-1}$ for the cyano group, as well as characteristic absorption bands for a monosubstituted aromatic ring. Further proof of structure was provided by the nmr spectrum which displayed a two-proton multiplet at delta 7.28 and a three-proton multiplet at delta 6.98 (aromatic), a one-proton multiplet at delta 4.56 (NCHCN), one-proton multiplets at delta 3.40 and 2.97 ($CH_2CH_2N$) and a six-proton multiplet at delta 2.71 which is assigned to the remainder of the piperidine ring.

We claim:
1. A process comprising the steps of:
    (a) reacting an N-substituted lactam having the formula:

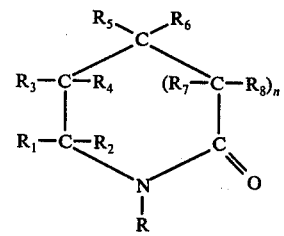

Wherein:
    $n$ is 0 to 1;
    R is methyl or phenyl; $R_1$ is H or pyridyl; and each of $R_2$ through $R_8$ is H with a reducing agent selected from the group consisting of sodium aluminum hydride, sodium bis-(methoxyethoxy)aluminum hydride and di-isobutylaluminum hydride at a temperature below about 20° C for at least 30 minutes under an inert atmosphere to produce an intermediate and (b) then reacting said intermediate with a reagent comprising an alkali metal cyanide at a temperature from about 0° to about 30° C for at least 15 minutes.

2. The process of claim 1, wherein the reaction of steps (a) and (b) are performed in a liquid solvent for the lactam.

3. The process of claim 2, wherein the solvent is tetrahydrofuran.

4. The process of claim 1, wherein the reaction of step (b) is conducted in the presence of ammonium ion.

5. The process of claim 4, wherein the intermediate is reacted with a reagent comprising potassium cyanide and ammonium chloride.

6. The process of claim 1, wherein the lactam is l-cotinine.

7. A product consisting essentially of 1-5'-cyanonicotine or an acid addition salt thereof.

8. A solution comprising a solvent containing at least 1% by total weight of the product of claim 7.

9. The solution of claim 8, wherein the solvent is water.

10. The process of claim 1, wherein R is methyl and $R_1$ is 3-pyridyl.

* * * * *